United States Patent [19]

Heinemann et al.

[11] Patent Number: 6,103,717
[45] Date of Patent: Aug. 15, 2000

[54] HALOGEN PYRIMIDINES AND ITS USE THEREOF AS PARASITE ABATEMENT MEANS

[75] Inventors: Ulrich Heinemann, Leichlingen; Herbert Gayer, Monheim; Peter Gerdes, Aachen; Bernd-Wieland Krüger, Bergisch Gladbach; Bernd Gallenkamp, Wuppertal; Uwe Stelzer, Burscheid; Albrecht Marhold; Ralf Tiemann, both of Leverkusen; Stefan Dutzmann, Langenfeld; Gerd Hänssler, Leverkusen; Klaus Stenzel, Düsseldorf, all of Germany

[73] Assignee: Bayer Aktiengesellschaft, Leverkusen, Germany

[21] Appl. No.: 09/101,791

[22] PCT Filed: Jan. 15, 1997

[86] PCT No.: PCT/EP97/00151

§ 371 Date: Jul. 16, 1998

§ 102(e) Date: Jul. 16, 1998

[87] PCT Pub. No.: WO97/27189

PCT Pub. Date: Jul. 31, 1997

[30] Foreign Application Priority Data

Jan. 22, 1996 [DE] Germany .............. 196 02 095

[51] Int. Cl.$^7$ ............ A01N 43/88; C07D 413/12; C07D 413/14

[52] U.S. Cl. ............ 514/229.2; 544/65; 544/319; 514/269

[58] Field of Search ............... 544/65, 319; 514/229.2, 514/269

[56] References Cited

U.S. PATENT DOCUMENTS 5,679,676  10/1997  Krüger et al. .............. 514/229.2
5,852,013  12/1998  Gerdes et al. .............. 514/229.2

FOREIGN PATENT DOCUMENTS 44 08 005   2/1995  Germany .
195 01 842  7/1996  Germany .

*Primary Examiner*—Mukund J. Shah
*Assistant Examiner*—Sudhaker B. Patel
*Attorney, Agent, or Firm*—Norris McLaughlin & Marcus

[57] ABSTRACT

Compounds of the formula (I)

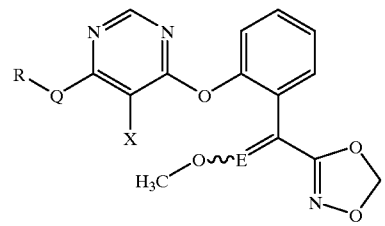

(I)

in which

A represents optionally substituted alkanediyl,

R represents in each case optionally substituted cycloalkyl, aryl or benzo-fused heterocyclyl, E represents —CH= or nitrogen, Q represents oxygen, sulphur, —CH$_2$—O—, a single bond, or a nitrogen atom which is optionally substituted by alkyl, and X represents halogen.

10 Claims, No Drawings

HALOGEN PYRIMIDINES AND ITS USE THEREOF AS PARASITE ABATEMENT MEANS

This application is a 371 of PCT/EP97100151, filed Jan. 15, 1997.

This invention relates to new halogenopyrimidines, to a process for their preparation, and to their use as pesticides.

Certain pyrimidines which have a similar substitution pattern have already been disclosed (WO-A 9504728).

However, the activity of these prior-art compounds is not entirely satisfactory in all fields of application, in particular when low rates and concentrations are applied.

There have now been found the new halogenopyrimidines of the general formula (I)

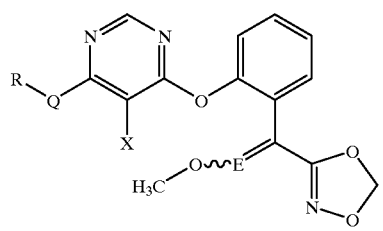

(I)

in which
A represents optionally substituted alkanediyl,
R represents in each case optionally substituted cycloalkyl, aryl or benzo-fused heterocyclyl,
E represents —CH= or nitrogen,
Q represents oxygen, sulphur, —CH$_2$—O—, a single bond, or a nitrogen atom which is optionally substituted by alkyl, and
X represents halogen.

Furthermore, it has been found that the new halogenopyrimidines of the general formula (I) are obtained when
a) hydroxy compounds of the general formula (II)

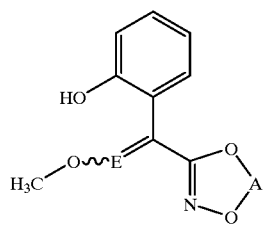

(II)

in which
A and E have the abovementioned meanings,
are reacted with a substituted halogenopyrimidine of the general formula (III)

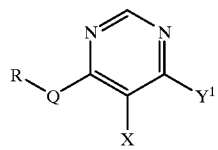

(III)

in which
R, Q and X have the abovementioned meanings and
$Y^1$ represents halogen,
if, appropriate in the presence of a diluent, if appropriate in the presence of an acid acceptor and if appropriate in the presence of a catalyst, or when
b) phenoxypyrimidines of the general formula (IV)

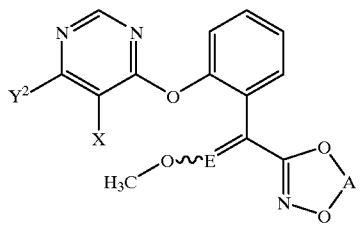

(IV)

in which
A, E and X have the abovementioned meanings and
$Y^2$ represents halogen
are reacted with a cyclic compound of the general formula (V)

$$R\text{—}Q\text{—}H \qquad (V)$$

in which
R and Q have the abovementioned meanings,
if appropriate in the presence of a diluent, if appropriate in the presence of an acid acceptor and if appropriate in the presence of a catalyst.

Finally, it has been found that the new halogenopyrimidines of the general formula (I) have a very powerful fungicidal activity.

Where appropriate, the compounds according to the invention can exist in the form of mixtures of various isomeric forms which are possible, in particular of stereoisomers, such as, for example, E and Z isomers. Claimed are not only the E and the Z isomers, but also any mixtures of these isomers.

The invention preferably relates to compounds of the formula (I) in which
A represents alkanediyl having 1 to 5 carbon atoms which is optionally substituted by halogen,
R represents cycloalkyl having 3 to 7 carbon atoms which is in each case optionally monosubstituted to disubstituted by halogen, alkyl or hydroxyl;
or represents benzodioxanyl which is optionally substituted by alkyl having 1 to 4 carbon atoms;
or represents phenyl or naphthyl, each of which is optionally monosubstituted to tetrasubstituted by identical or different substituents, other substituents which are possible preferably being selected from amongst the enumeration which follows:
halogen, cyano, nitro, amino, hydroxyl, formyl, carboxyl, carbamoyl, thiocarbamoyl;
in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl, each of which has 1 to 8 carbon atoms;
in each case straight-chain or branched alkenyl or alkenyloxy, each of which as 2 to 6 carbon atoms;
in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;
in each case straight-chain or branched halogenoalkenyl or halogenoalkenyloxy, each of which has 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alenylcarbonyl or alkinylcarbonyl, each of which has 1 to 6 carbon atoms in the respective hydrocarbon chains;

cycloalkyl or cycloalkyloxy, each of which has 3 to 6 carbon atoms;

alkylene having 3 or 4 carbon atoms, oxyalkylene having 2 or 3 carbon atoms or dioxyalkylene having 1 to 2 carbon atoms, in each case optionally monosubstituted to tetrasubstituted by identical or different substituents from the series consisting of fluorine, chlorine, oxo, methyl, trifluoromethyl or ethyl;

or a group

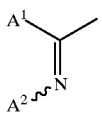

where
A¹ represents hydrogen, hydroxyl or alkyl having 1 to 4 carbon atoms or cycloalkyl having 1 to 6 carbon atoms and
A² represents hydroxyl, amino, methylamino, phenyl, benzyl, or represents alkyl or alkoxy having 1 to 4 carbon atoms, each of which is optionally substituted by cyano, hydroxy, alkoxy, alkylthio, alkylamino, dialkylamino or phenyl, or represents alkenyloxy or alkinyloxy, each of which has 2 to 4 carbon atoms,
and also phenyl, phenoxy, phenylthio, benzoyl, benzoylethenyl, cinnamoyl, heterocyclyl, phenylalkyl, phenylalkyloxy, phenylalkylthio or heterocyclylalkyl, each of which has 1 to 3 carbon atoms in the respective alkyl moieties and each of which is optionally monosubstituted to trisubstituted in the cyclic moiety by halogen and/or straight-chain or branched alkyl or alkoxy having 1 to 4 carbon atoms,
E represents —CH═ or nitrogen,
Q represents oxygen, sulphur, a single bond or a nitrogen atom which is optionally substituted by methyl, ethyl or n- or i-propyl and
X represents fluorine, chlorine, bromine or iodine.

In the definitions, the saturated or unsaturated hydrocarbon chains, such as alkyl, alkanediyl, alkenyl or alkinyl, also together with hetero atoms, such as, for example, in alkoxy, alkylthio or alkylamino, are in each case straight-chain or branched.

In particular, the invention relates to compounds of the formula (I) in which
A represents methylene, ethane-1,1-diyl, ethane-1,2-diyl, propane-1,1-diyl, propane-1,2-diyl, propane-1,3-diyl, butane-1,1-diyl, butane-1,2-diyl, butane-1,3-diyl or butane-2,2-diyl, each of which is optionally substituted by fluorine or chlorine,
represents cyclopentyl or cyclohexyl, each of which is optionally monosubstituted to disubstituted by fluorine, chlorine, methyl, ethyl or hydroxyl;
or represents benzodioxanyl which is optionally substituted by methyl or ethyl;
or represents phenyl or naphthyl, each of which is optionally monosubstituted to tetrasubstituted by identical or different substituents, the substituents which are possible preferably being selected from amongst the enumeration which follows:

fluorine, chlorine, bromine, iodine, cyano, nitro, amino, hydroxyl, formyl, carboxyl, carbamoyl, thiocarbamoyl, methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl, methoxy, ethoxy, n- or i-propoxy, methylthio, ethylthio, n- or i-propylthio, methylsulphinyl, ethylsulphinyl, methylsulphonyl or ethylsulphonyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

Trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, acryloyl, propioloyl, cyclopentyl, cyclohexyl, in each case divalent propanediyl, ethyleneoxy, methylenedioxy, ethylenedioxy, each of which is optionally monosubstituted to tetrasubstituted by identical or different substituents from the series consisting of fluorine, chlorine, oxo, methyl or trifluoromethyl, or a group

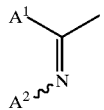

where
A¹ represents hydrogen, methyl or hydroxyl and
A² represents hydroxyl, methoxy, ethoxy, amino, methylamino, phenyl, benzyl or hydroxyethyl, and
phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2yl, benzimidazol-2-yl, dioxol-2-yl, oxadiazolyl, each of which is optionally monosubstituted to trisubstituted in the cyclic moiety by halogen and/or straight-chain or branched alkyl or alkoxy having 1 to 4 carbon atoms,
E represents —CH═ or nitrogen,
Q represents oxygen, sulphur, a single bond or a nitrogen atom which is optionally substituted by methyl, and
X represents fluorine or chlorine.

The definitions of radicals given above in general or in preferred ranges apply both to the end products of the formula (I) and, analogously, to the starting materials or intermediates required in each case for the preparation.

Independently of the combination given in each case, the definitions of radicals given individually for these radicals in the respective combinations or preferred combinations of radicals are also replaced by definitions of radicals of other preferred ranges as required.

Formula (II) provides a general definition of the hydroxy compounds required as starting materials for carrying out Process a) according to the invention. In this formula (II), A and E preferably, or in particular, have thsoe meanings which have already been given in connection with the description of the compounds of the formula (I) according to the invention as being preferred, or particularly preferred, for A and E.

Some of the starting materials of the formula (II) are known, and/or they can be prepared by processes known per se (cf. WO-A 9504728). New, and also the subject of the present application, are methoxyvinyl compounds of the general formula (IIa)

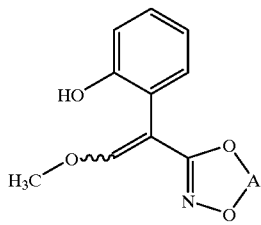

(IIa)

in which

A has the abovementioned meaning.

The methoxyvinyl compounds of the formula (IIa) are obtained when (Process a-1) tetrahydropyranylethers of the general formula (VI)

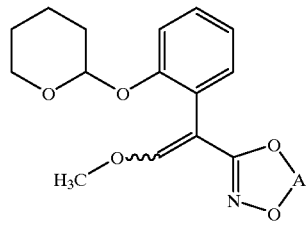

(VI)

in which

A has the abovementioned meaning, are treated with an acid, preferably an inorganic or organic protonic or Lewis acid, such as, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as the etherate), boron tribromide, aluminum trichloride, zinc chloride, iron(III) chloride, antimony pentachloride, or else with a polymeric acid such as, for example, an acidic ion exchanger, an acidic aluminum oxide or acidic silica gel, at temperatures from −20° C. to 120° C., preferably at temperatures from −10° C. to 80° C., if appropriate in the presence of a diluent, preferably an ether, such as diethyl ether, diisopropyl ether, methyl t-butyl ether, methyl t-amyl ether, dioxane, tetrahydrofuran, 1,2-dimethoxyethane, 1.2-diethoxyethane or anisole; a sulphoxide, such as dimethyl sulphoxide; a sulphone, such as sulpholane; an alcohol such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water, or pure water.

Formula (VI) provides a general definition of the tetrahydropyranyl ethers required as starting materials for carrying out Process a-1) according to the invention. In this formula (VI), A preferably, or in particular, has the meaning which has already been given in connection with the description of the compounds of the formula (I) according to the invention as being preferred, or particularly preferred, for A.

The starting materials of the formula (VI) are new and also a subject of the present application.

The tetrahydropyranol ethers of the formula (VI) are obtained when (Process a-2) keto compounds of the general formula (VII)

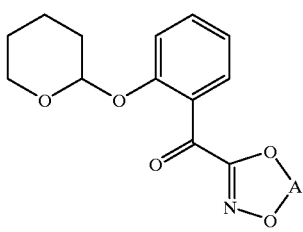

(VII)

in which

A has the abovementioned meaning, are reacted with methoxymethyl-triphenyl-phosphonium chloride, bromide or iodide, if appropriate in the presence of a diluent, preferably an inert aprotic solvent such as, for example, an ether such as diethyl ether, diisopropyl ether, methyl t-butyl ether, methyl t-amyl ether, dioxane, tetrahydrofuran, 1,2-dimethoxyethane, 1,2-diethoxyethane or anisole; an amide such as N,N-dimethylformamide, N,N-dimethylacetamide, N-methylformanilide, N-methylpyrrolidone or hexamethylphosphoric triamide; a sulphoxide such as dimethyl sulphoxide, or of a sulphone such as sulpholane, and if appropriate in the presence of a base, preferably of an alkaline earth metal hydride, hydroxide, amide or alcoholate or of an alkali metal hydride, hydroxide, amide or alcoholate such as, for example, sodium hydride, sodium amide, sodium methoxide, sodium ethoxide, potassium tert-butoxide, sodium hydroxide or potassium hydroxide, at temperatures from 0° C. to 100° C., preferably from 20° C. to 80° C.

Formula (VII) provides a general definition of the keto compounds required as starting materials for carrying out Process a-2) according to the invention. In this formula (VII), A preferably, or in particular, has the meaning which has already been given in connection with the description of the compounds of the formula (I) according to the invention as being preferred, or particularly preferred, for A.

The starting materials of the formula (VII) are new and also a subject of the present application.

The keto compounds of the formula (VII) are obtained when (Process a-3) halogenophenyl compounds of the general formula (VIII)

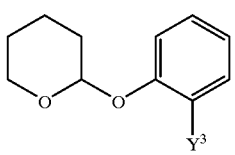

(VIII)

in which
Y³ represents halogen
are reacted with amides of the formula (IX)

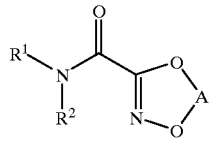
(IX)

in which
A has the abovementioned meaning and
R¹ and R² are identical or different and represent alkyl, or together with the nitrogen atom to which they are bonded represent a 3- to 8-membered saturated heterocyclic ring,
at temperatures from −80 to 20° C., preferably −60 to −20° C.,
if appropriate in the presence of a diuluent, preferably an aliphatic, alicyclic or aromatic hydrocarbon such as, for example, petroleum ether, hexane, heptane, cyclohexane, methylcyclohexane, benzene, toluene, xylene or decalin, or of an ether such as diethyl ether, diisopropyl ether, methyl t-butyl ether, methyl t-amyl ether, dioxane, tetrahydrofuran, 1,2-dimethoxyethane, 1,2-diethoxyethane or anisole and
if appropriate in the presence of a base, preferably, an alkaline earth metal hydride or amide or alkali metal hydride or amide, such as, for example, sodium hydride or sodium amide, or of an alkali metal hydrocarbon compound or alkaline earth metal hydrocarbon compound, such as butyllithium.

Formula (VIII) provides a general definition of the halogenophenyl compounds required as starting materials for carrying out Process a-3) according to the invention. In this formula (VIII), Y³ represents halogen, preferably bromine.

The starting materials of the formula (VIII) are known, and/or they can be prepared by known methods (compare, for example, Synthesis 1987, 951).

Formula (IX) provides a general definition of the amides furthermore required as starting materials for carrying out Process a-3) according to the invention. In this formula (IX), A preferably, or in particular, has the meaning which has already been given in connection with the description of the compounds of the formula (I) according to the invention as being preferred, or particularly preferred, for A. R¹ and R² are identical or different and represent alkyl, preferably methyl, ethyl, n- or i-propyl or n-, i-, s- or t-butyl, or together with the nitrogen atom to which they are bonded represent a 3- to 8-membered saturated heterocyclic ring, preferably azetidinyl, pyrrolidinyl, morpholinyl, piperidinyl, hexahydroazepinyl.

The starting materials of the formula (IX) are new and also an object of the present application.

The amides of the formula (IX) are obtained when (Process a-4) oxamates of the general formula (X)

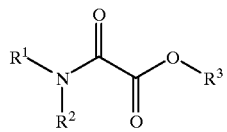
(X)

in which
R¹ and R² have the abovementioned meanings and
R³ represents alkyl,
are first reacted with hydroxylamine or with an acid addition salt thereof, if appropriate in the presence of a diluent, preferably of an alcohol such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monethyl ether,
and if appropriate in the presence of a base, preferably of an alkaline earth metal hydroxide, alcoholate, acetate, carbonate or hydrogen carbonate, such as, for example, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogen carbonate or sodium hydrogen carbonate,
at temperatures from −20 to 50° C., preferably 0 to 40° C., and the resulting hydroxamic acid of the formula (XI)

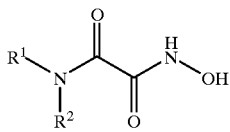
(XI)

with working up, is reacted with an alkylene derivative of the general formula (XII)

Y⁴—A—Y⁵ (XII)

in which
A has the abovementioned meaning and
Y⁴ and⁵ are identical or different and represent halogen, alkylsulphonyl or arylsulphonyl,
if appropriate in the presence of a diluent, preferably of an alcohol, and if appropriate in the presence of a base, preferably of an alkaline earth metal hydroxide, alcoholate, acetate, carbonate or hydrogen carbonate, such as, for example, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogen carbonate or sodium hydrogen carbonate.

Formula (X) provides a general definition of the oxalamidates required as starting materials for carrying out the first step of process a-4) according to the invention. In this formula (X), R¹ and R² preferably, or in particular, have those meanings which have already been given in connection with the description of the compounds of the formula (IX) according to the invention as being preferred, or particularly preferred for R¹ and R², R³ represents alkyl, preferably methyl or ethyl.

The starting materials of the formula (X) are known, and/or they can be prepared by known methods (compare, for example, EP-A 469889)

Hydroxylamine or salts thereof, which are further more required for carrying out the first step of Process a-4) according to the invention, are generally customary chemicals for synthesis.

Formula (XII) provides a general definition of the alkylene derivatives required as starting materials for carrying out the second step of Process a-4) according to the invention. In this formula (XII), A preferably, or in particular, has the meaning which has already been given in connection with the description of the compounds of the formula (I) according to the invention as being preferred, or particularly preferred, for A. $Y^4$ and $Y^5$ are identical or different and represent halogen, preferably chlorine or bromine; alkylsulphonyl, preferably methanesulphonyl; or arylsulphonyl, preferably toluenesulphonyl.

Formula (III) provides a general definition of the halogenopyrimidines furthermore required as starting materials for carrying out Process a) according to the invention. In this formula (III), R, Q and X preferably, or in particular, have the meanings which have already been given in connection with the description of the compounds of the formula (I) according to the invention as being preferred, or particularly preferred, for R, Q and X. $Y^1$ represents halogen, preferably fluorine or chlorine.

The starting materials of the formula (III) are known, and/or they can be prepared by known methods (compare, for example, DE-A 4340181; Chem Ber., 90 <1957>942, 951).

Formula (IV) provides a general definition of the phenoxypyrimidines required as starting materials for carrying out Process b) according to the invention. In this formula (IV), A, E and X preferably, or in particular, have the meanings which have already been given in connection with the description of the compounds of the formula (I) according to the invention as being preferred, or particularly preferred, for A, E and X. $Y^2$ represents halogen, preferably fluorine or chlorine.

The starting materials of the formula (IV) are new and also the subject of the present invention.

The phenoxypyrimidines of the general formula (IV) are obtained (Process b-1) when hydroxy compounds of the general formula (II) are reacted with a trihalogenopyrimidine of the general formula (XIII)

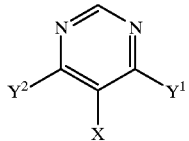

(XIII)

in which

X, $Y^1$ and $Y^2$ are identical or different and represent in each case halogen, if appropriate in the presence of a diluent, if appropriate in the presence of an acid acceptor and if appropriate in the presence of a catalyst.

The hydroxy compounds of the formula (II) required as starting materials for carrying out Process b-1) according to the invention have already been described in connection with the description of Process a) according to the invention.

Formula (XIII) provides a general definition of the trihalogenopyrimidines furthermore required as starting materials for carrying out Process b-1) according to the invention. In this formula (XIII), X, $Y^1$ and $Y^2$ represent halogen, preferably fluorine or chlorine.

The trihalogenopyrimidines are known, and/or they can be prepared by known methods (compare, for example, Chesterfield et al., J. Chem Soc., 1955; 3478, 3480).

Formula (V) provides a general definition of the cyclic compounds furthermore required as starting materials for carrying out Process b) according to the invention. In this formula (V), R and Q preferably, or in particular, have the meanings which have already been given in connection with the description of the compounds of the formula (I) as being preferred, or particularly preferred, for R and Q.

The cyclic compounds of the formula (V) are known chemicals for synthesis or can be prepared by simple methods.

Diluents which are suitable for carrying out Processes a), b) and b1), according to the invention are all inert organic solvents. These preferably include ethers such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile, amides such as N,N-dimethylformamide, N,N-dimethylacetamide, N-methylformanilide, N-methylpyrrolidone or hexamethylphosphoric triamide; sulphoxides, such as dimethyl sulphoxide; or sulphones such as sulpholane.

If appropriate, Processes a), b) and b-1) according to the invention are carried out in the presence of a suitable acid acceptor. Suitable acid acceptors are all customary inorganic or organic bases. These preferably include alkaline earth-metal hydrides, hydroxides, alcoholates, carbonates or hydrogen carbonates or alkali metal hydrides, hydroxides, alcoholates, carbonates or hydrogen carbonates such as, for example, sodium hydride, sodium amide, potassium tert-butoxide, sodium hydroxide, potassium hydroxide, sodium carbonate, potassium carbonate, potassium hydrogen carbonate or sodium hydrogen carbonate.

Suitable catalysts for Processes a), b) and b-1) according to the invention are all copper(I) salts, such as, for example, copper(I) chloride, copper(I) bromide or copper(I) iodide.

When carrying out Processes a), b) and b-1) according to the invention, the reaction temperatures can be varied within a substantial range. In general, the processes are carried out at temperatures from –20° C. to 100° C., preferably at temperatures from –10° C. to 80° C.

All the processes according to the invention are generally carried out under atmospheric pressure. However, it is also possible to carry out the processes under elevated or reduced pressure, in general between 0.1 bar and 10 bar.

The reaction is carried out and the reaction products are worked up and isolated by generally customary methods (compare also the preparation examples).

The active compounds according to the invention have a powerful microbicidal activity and can be employed in practice for controlling undesirable microorganisms. The active compounds are suitable for use as crop protection agents, in particular as fungicides.

Fungicidal agents are employed in crop protection for controlling Plasmodiophoromycetes, Oomycetes, Chytridiomycetes, Zygomycetes, Ascomycetes, Basidiomycetes and Deuteromycetes.

Bactericidal agents are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation.

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli,* or *Psudoperonospora cubensis;*

Plasmopara species, such as, for exampsle, *Plasmopara viticola;*

Bremia species, such as, for example, *Bremia lactucae*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria braccicae* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds are employed particularly successfully for controlling cereal diseases, such as, for example, against Erysiphe, Fusarium, Pseudocercosporella and Puccinia species, or for controlling diseases in viticulture or fruit and vegetable production, such as, for example, against Venturai, Sphaerotheca, Phytophthora and Plasmopara species, or else for controlling rice diseases, such as, for example, Pyricularia species. Furthermore, the active compounds according to the invention have a very powerful and broad in-vitro activity.

Depending on their particular physical and/or chemical properties, the active compounds can be converted into the customary formulations, such as solutions, emulsions, suspensions, powdeers, foams, pastes, granules, aerosols, microencapsulations in polymeric substances and in coating compositions for seed, or else ULV cold- and hot-fogging formulations.

These formulations are produced in a known manner, for example by mixing the active compounds with extenders, that is, liquid solvents, liquefield gases under pressure, and/or solid carriers, optionally with the use of surface-active agents, that is, emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzens, chloroethylenes or methylene chloride, aliphatic hydrocarbons such as cyclohexane or parafffins, for example mineral oil fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as halogenohydrocarbons, or else butane, propane, nitrogen and carbon dioxide. Suitable solid carriers are for example ground natural minerals such as kolins, clays, talc, chalk, quartz, attapulgite, montmorillonite or diatomaceous earth, and ground synthetic minerals such as highly-disperse silica, alumina and silicates. Suitable solid carriers for granules are for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers, are for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations can also be used as a mixture with known fungicides, bactericides, acaricides, nematicides or insecticides, for example to widen the spectrum of action or to prevent the build-up of resistance. In many cases, synergistic effects are obtained, i.e. the activity of the mixture is greater than the activity of the individual components.

Examples of particularly advantageous mixtures are the following compounds.

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5- carboxanilide; 2,6-dichloro-N-(4-trifluoromethylbenzl) benzamide; (E)-2-methoxyimino-N-methyl-2-(2-phenoxyphenyl)acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl] acetate; 2-phenylphenol (OPP), aldimorph, ampropylfos, anilazine, azaconazole, benalaxyl, benodanil, benomyl, binapacryl, biphenyl, bitertanol, blasticidin-S, bromoconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol. fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencyuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin,

*Bacillus thuringiensis,* 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chloroethoxyfos, chlorofenvinphos, chlorofluazuron, chloromephos, N-[(6-chloro-3-pyridinyl)-methyl]-N'-cyano-N-methyl-ethanimidamide, chloropyrifos, chloropyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, difenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenzaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides or with fertilizers or growth regulators is also possible.

The active compounds can be used as such, in the form of their commercially available formulations or the use forms prepared therefrom, such as read-to-use solutions, suspensions, wettable powders, pastes, soluble powders, dusts and granules. They are used in the customary manner, for example by pouring, spraying, atomizing, scattering, foaming, brushing on and the like. It is also possible to apply the active compounds by the ultra-low volume method, or to inject the active compound formulation or the active compound itself into the soil. The seed of the plants can also be treated.

In the treatment of parts of plants, the active compound concentrations in the use forms can be varied within a substantial range: They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the site of action.

PREPARATION EXAMPLES

Example 1

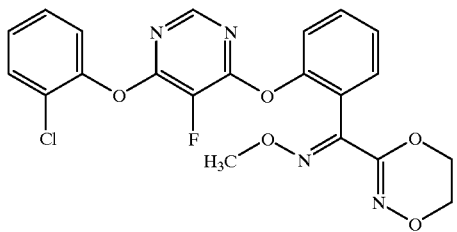

Process a)

136.8 g (0.56 mol) of 4-(2-chlorophenoxy)-5,6-difluoropyrimidine are added all at once to a mixture of 135.3 g (0.56 mol) of 3-[1-(2-hydroxyphenyl)-1-(methoximino)-methyl]-5,6-dihydro-1,4,2-dioxazine and 197.6 of ground potassium carbonate in 460 ml of acetonitrile at 20° C., during which process the temperature rises to 31° C. The mixture is stirred for a further 6 hours at 50° C. and then without further heating overnight, during which process the mixture cools. The reaction mixture is added to 2.3 l of ice-water and stirred for 5 hours, the product crystallizing out. This product is filtered off with suction and washed with 0.57 l of water in portions. 260 g (97.8% of theory) of 3-{1-[2-(4-<2-chlorophenoxy>-5-fluoropyrimid-6-yloxy)-phenyl]-1-(methoximino)-methyl}-5,6-dihydro-1, 4,2-dioxazine of melting point 75° C. are obtained.

Example 2

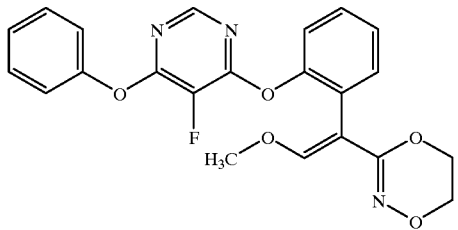

Process a)

0.119 g of potassium hydride (60% suspension in mineral oil) is added to a solution of 0.7 g (0.00298 mol) of 3-[1-(2-hydroxyphenyl)-2-methoxyethen-1-yl]-5,6-dihydro-1,4,2-dioxazine and 0.6 g (0.00288 mol) of 4-phenoxy-5,6-difluoropyrimidine in 10 ml of dimethylformamide at 0° C., and the mixture is then stirred for 12 hours at 20° C. The reaction mixture is poured into water and extracted using ethyl acetate. The combined organic phases are dried over sodium sulphate and concentrated under reduced pressure. The residue is chromatographed on silica gel using cyclohexane/ethyl acetate (1:1). 0.4 g (82% of theory) of 3-{1-[2-(4-phenoxy-5-fluoropyrimid-6-yloxy)-phenyl]-2-methoxyethen-1-yl}-5,6-dihydro-1,4,2-dioxazine is obtained.

$^1$H NMR spectrum (CDCl$_3$/TMS): δ=3.678 (3H); 4.056/4.069/4.083 (2H); 4.300/4.314/4.328 (2H); 6.891 (1H); 7.199–7.475 (9H); 8.063 (1H) ppm.

Example 3

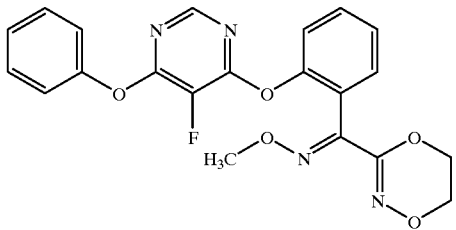

Process b)

A mixture of 124.1 g (0.333 mol) of 3-{1-[2-(4,5-difluoropyrimid-6-yloxy)-phenyl]-1-(methoximino)-methyl}-5,6-dihydro-1,4,2-dioxazine, 31.3 g (0.333 mol) of phenol, 46 g (0.333 of potassium carbonate and 3.3 g of copper(I) chloride in 1 l of dimethylformamide is stirred overnight at 100° C. After the mixture has cooled to 20° C., the solvent is distilled off under reduced pressure. The residue is taken up in ethyl acetate and washed repeatedly using water. The organic phase is dried over sodium sulphate and reconcentrated under reduced pressure. The residue is chromatographed on silica gel using hexane/acetone (7:3). 112.4 g (97% of theory) of 3-{1-[2-(4-phenoxy-5-fluoropyrimid-6-yloxy)-phenyl]-1-(methoximino)-methyl}-5,6-dihydro-1,4,2-dioxazine of melting point 110° C. are obtained.

The compounds of the formula (I) mentioned in Table 1 below are obtained analogously to Examples 1 to 3 and following the information given in the general description of the process.

TABLE 1
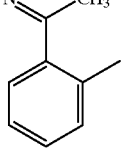
(I)
| Ex. No. | R | Q | X | E | A | Phys. data |
|---|---|---|---|---|---|---|
| 4 | 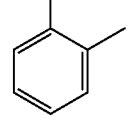 | O | F | N | —CH$_2$—CH$_2$— | NMR*: 3.85 (s, 3H) |
| 5 | 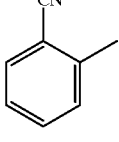 | O | F | N | —CH$_2$—CH$_2$— | NMR*: 3.85 (s, 3H) |
| 6 | 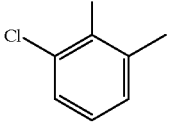 | O | F | N | —CH$_2$—CH$_2$— | m.p.: 135° C. |
| 7 | 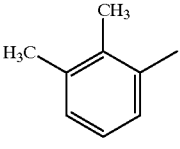 | O | F | N | —CH$_2$—CH$_2$— | NMR*: 3.80 (s, 3H) |
| 8 | 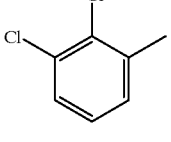 | O | F | N | —CH$_2$—CH$_2$— | NMR*: 3.85 (s, 3H) |
| 9 | 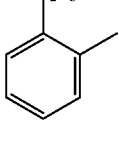 | S | F | N | —CH$_2$—CH$_2$— | NMR*: 3.80 (s, 3H) |
| 10 |  | O | F | N | —CH$_2$—CH$_2$— | NMR*: 3.85 (s, 3H) |

TABLE 1-continued (I)

| Ex. No. | R | Q | X | E | A | Phys. data |
|---|---|---|---|---|---|---|
| 11 | 2-methyl-(OCHF₂)phenyl | O | F | N | —CH₂—CH₂— | NMR*: 3.85 (s, 3H) |
| 12 | 2-methyl-(NO₂)phenyl | O | F | N | —CH₂—CH₂— | NMR*: 3.85 (s, 3H) |
| 13 | 3-(CF₃)-methylphenyl | O | F | N | —CH₂—CH₂— | NMR*: 3.85 (s, 3H) |
| 14 | 2,4,6-trimethylphenyl | O | F | N | —CH₂—CH₂— | NMR*: 3.85 (s, 3H) |
| 15 | 2-methyl-(Br)phenyl | O | F | N | —CH₂—CH₂— | NMR*: 3.80 (s, 3H) |
| 16 | 2-methyl-(isopropyl)phenyl | O | F | N | —CH₂—CH₂— | NMR*: 3.80 (s, 3H) |
| 17 | 2-methyl-(F)phenyl | O | F | N | —CH₂—CH₂— | NMR*: 3.85 (s, 3H) |

TABLE 1-continued (I)

| Ex. No. | R | Q | X | E | A | Phys. data |
|---|---|---|---|---|---|---|
| 18 | OC₂H₅ (2-methylphenyl) | O | F | N | —CH₂—CH₂— | NMR*: 3.80 (s, 3H) |
| 19 | SC₂H₅ (2-methylphenyl) | O | F | N | —CH₂—CH₂— | NMR*: 3.80 (s, 3H) |
| 20 | cyclopentyl-(2-methylphenyl) | O | F | N | —CH₂—CH₂— | NMR*: 3.85 (s, 3H) |
| 21 | Cl (2-methylphenyl) | NH | F | N | —CH₂—CH₂— | NMR*: 3.85 (s, 3H) |
| 22 | 2-F, 4-Cl-methylphenyl | O | F | N | —CH₂—CH₂— | NMR*: 3.80 (s, 3H) |
| 23 | OCF₃ (2-methylphenyl) | O | F | N | —CH₂—CH₂— | NMR*: 3.85 (s, 3H) |
| 24 | 2-allyl-methylphenyl | O | F | N | —CH₂—CH₂— | NMR*: 3.85 (s, 3H) |

TABLE 1-continued
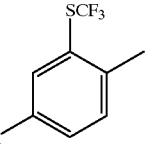
(I)
| Ex. No. | R | Q | X | E | A | Phys. data |
|---|---|---|---|---|---|---|
| 25 | 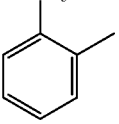 | O | F | N | —CH$_2$—CH$_2$— | NMR*: 3.85 (s, 3H) |
| 26 | 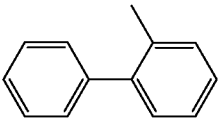 | O | F | N | —CH$_2$—CH$_2$— | NMR*: 3.85 (s, 3H) |
| 27 | 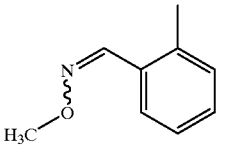 | O | F | N | —CH$_2$—CH$_2$— | NMR*: 3.70 (s, 3H) |
| 28 | 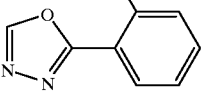 | O | F | N | —CH$_2$—CH$_2$— | NMR*: 3.85 (s, 3H) |
| 29 | 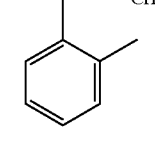 | O | F | N | —CH$_2$—CH$_2$— | NMR*: 3.85 (s, 3H) |
| 30 | 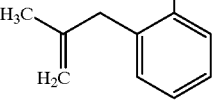 | O | F | N | —CH$_2$—CH$_2$— | NMR*: 3.80 (s, 3H) |
| 31 |  | O | F | N | —CH$_2$—CH$_2$— | NMR*: 3.85 (s, 3H) |

TABLE 1-continued (I)

| Ex. No. | R | Q | X | E | A | Phys. data |
|---|---|---|---|---|---|---|
| 32 | 2-(CF₃)-phenyl-CH₂- | O | F | N | —CH₂—CH₂— | NMR* 3.80 (s, 3H) |
| 33 | 2-(benzyloxy)-phenyl-CH₂- | O | F | N | —CH₂—CH₂— | NMR* 3.75 (s, 3H) |
| 34 | 2-(n-C₃H₇)-phenyl-CH₂- | O | F | N | —CH₂—CH₂— | NMR*: 3.85 (s, 3H) |
| 35 | 2-(Et₂NC(O)O)-phenyl-CH₂- | O | F | N | —CH₂—CH₂— | NMR*: 3.90 (s, 3H) |
| 36 | 2-cyclohexyl-phenyl-CH₂- | O | F | N | —CH₂—CH₂— | NMR*: 3.80 (s, 3H) |
| 37 | 2-(t-Bu)-phenyl-CH₂- | O | F | N | —CH₂—CH₂— | NMR*: 3.80 (s, 3H) |
| 38 | 2-(benzylthio)-phenyl-CH₂- | O | F | N | —CH₂—CH₂— | NMR*: 3.80 (s, 3H) |

TABLE 1-continued
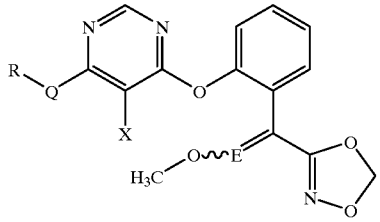
(I)
| Ex. No. | R | Q | X | E | A | Phys. data |
|---|---|---|---|---|---|---|
| 39 | 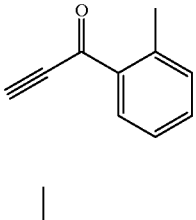 | O | F | N | —CH₂—CH₂— | NMR*: 3.85 (s, 3H) |
| 40 | 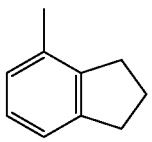 | O | F | N | —CH₂—CH₂— | NMR*: 3.85 (s, 3H) |
| 41 | 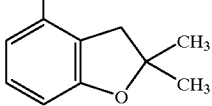 | O | F | N | —CH₂—CH₂— | NMR*: 3.85 (s, 3H) |
| 42 | 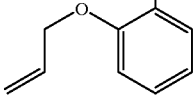 | O | F | N | —CH₂—CH₂— | NMR*: 3.80 (s, 3H) |
| 43 | 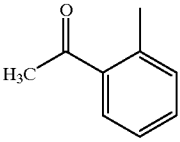 | O | F | N | —CH₂—CH₂— | NMR*: 3.85 (s, 3H) |
| 44 | 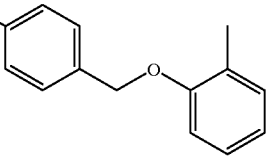 | O | F | N | —CH₂—CH₂— | NMR*: 3.85 (s, 3H) |
| 45 |  | O | F | N | —CH₂—CH₂— | NMR*: 3.80 (s, 3H) |

TABLE 1-continued
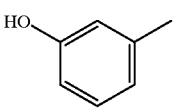
(I)
| Ex. No. | R | Q | X | E | A | Phys. data |
|---|---|---|---|---|---|---|
| 46 | 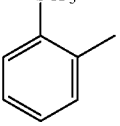 | O | F | N | —CH$_2$—CH$_2$— | NMR*: 3.85 (s, 3H) |
| 47 | 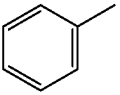 | O | F | N | —CH$_2$—CH$_2$— | NMR*: 3.85 (s, 3H) |
| 48 | 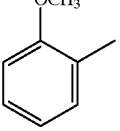 | —CH$_2$—O— | F | N | —CH$_2$—CH$_2$— | NMR*: 3.80 (s, 3H) |
| 49 | 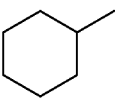 | O | F | N | —CH$_2$—CH$_2$— | NMR*: 3.80 (s, 3H) |
| 50 | 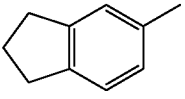 | O | F | N | —CH$_2$—CH$_2$— | NMR*: 3.85 (s, 3H) |
| 51 | 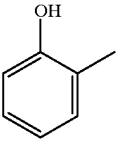 | O | F | N | —CH$_2$—CH$_2$— | m.p.: 168° C. |
| 52 | 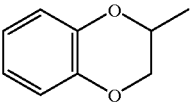 | O | F | N | —CH$_2$—CH$_2$— | m.p.: 192° C. |
| 53 | 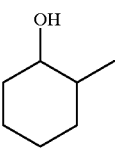 | —CH$_2$—O— | F | N | —CH$_2$—CH$_2$— | NMR*: 3.85 (s, 3H) |
| 54 |  | O | F | N | —CH$_2$—CH$_2$— | NMR*: 3.85 (s, 3H) |

TABLE 1-continued (I)

| Ex. No. | R | Q | X | E | A | Phys. data |
|---|---|---|---|---|---|---|
| 55 | (2-methylphenyl)-CH=CH-CH₃ | O | F | N | —CH₂—CH₂— | NMR*: 3.85 (s, 3H) |
| 56 | Ph-C(=O)-CH=CH-(2-methylphenyl) | O | F | N | —CH₂—CH₂— | NMR*: 3.85 (s, 3H) |
| 57 | (2-methylphenyl)-O-CH(CH₃)₂ | O | F | N | —CH₂—CH₂— | NMR*: 3.85 (s, 3H) |
| 58 | Ph-C(=O)-(2-methylphenyl) | O | F | N | —CH₂—CH₂— | NMR*: 3.80 (s, 3H) |
| 59 | 2-(2-methylphenyl)-5,5-dimethyl-1,3-dioxane | O | F | N | —CH₂—CH₂— | NMR*: 3.80 (s, 3H) |
| 60 | 2-(2-methylphenyl)-1H-benzimidazole | O | F | N | —CH₂—CH₂— | NMR*: 3.80 (s, 3H) |
| 61 | (2-methylphenyl)-CH(OCH₃)₂ | O | F | N | —CH₂—CH₂— | NMR*: 3.85 (s, 3H) |

TABLE 1-continued (I)

| Ex. No. | R | Q | X | E | A | Phys. data |
|---|---|---|---|---|---|---|
| 62 | [2-methyl-allyloxy-methyl attached to o-tolyl] | O | F | N | —CH₂—CH₂— | NMR*: 3.85 (s, 3H) |
| 63 | [benzyl attached to o-tolyl] | O | F | N | —CH₂—CH₂— | NMR*: 3.80 (s, 3H) |
| 64 | [4,5-dimethyl-1,3-dioxolan-2-yl attached to o-tolyl] | O | F | N | —CH₂—CH₂— | NMR*: 3.85 (s, 3H) |
| 65 | [N,N-dimethylbenzamide, o-methyl] | O | F | N | —CH₂—CH₂— | NMR*: 3.85 (s, 3H) |
| 66 | [hydrazone of o-methylacetophenone] | O | F | N | —CH₂—CH₂— | NMR*: 3.80 (s, 3H) |
| 67 | [HO-CH₂CH₂-N=CH- attached to o-tolyl] | O | F | N | —CH₂—CH₂— | NMR*: 3.85 (s, 3H) |
| 68 | [PhN=CH- attached to o-tolyl] | O | F | N | —CH₂—CH₂— | NMR*: 3.85 (s, 3H) |

TABLE 1-continued (I)

| Ex. No. | R | Q | X | E | A | Phys. data |
|---|---|---|---|---|---|---|
| 69 | *N-benzyl-2-methylbenzamide* | O | F | N | —CH₂—CH₂— | NMR*: 3.70 (s, 3H) |
| 70 | *(E)-1-(2-methylphenyl)-3-phenylprop-2-en-1-one* | O | F | N | —CH₂—CH₂— | NMR*: 3.75 (s, 3H) |
| 71 | *1-(2-methylbenzyl)-1H-1,2,4-triazole* | O | F | N | —CH₂—CH₂— | NMR*: 3.85 (s, 3H) |
| 72 | *1-methyl-2-(2-methylphenyl)-1H-benzimidazole* | O | F | N | —CH₂—CH₂— | NMR*: 3.75 (s, 3H) |
| 73 | *4-(2-methylphenyl)butan-2-one* | O | F | N | —CH₂—CH₂— | NMR*: 3.85 (s, 3H) |
| 74 | *N-benzyl-1-(2-methylphenyl)methanimine* | O | F | N | —CH₂—CH₂— | NMR*: 3.85 (s, 3H) |
| 75 | *methyl 2-methylbenzoate* | O | F | N | —CH₂—CH₂— | NMR*: 3.85 (s, 3H) |

TABLE 1-continued
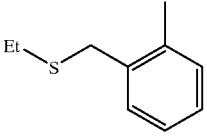
(I)
| Ex. No. | R | Q | X | E | A | Phys. data |
|---|---|---|---|---|---|---|
| 76 | 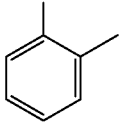 | O | F | N | —CH$_2$—CH$_2$— | NMR*: 3.85 (s, 3H) |
| 77 | 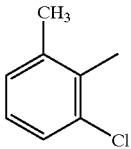 | O | F | N | —CH$_2$—CH$_2$— | NMR*: 3.85 (s, 3H) |
| 78 | 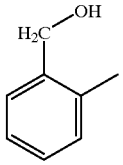 | O | F | N | —CH$_2$—CH$_2$— | NMR*. 3.85 (s, 3H) |
| 79 | 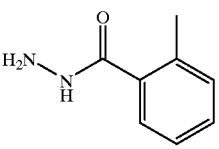 | O | F | N | —CH$_2$—CH$_2$— | NMR*: 3.85 (s, 3H) |
| 80 | 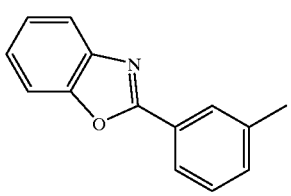 | O | F | N | —CH$_2$—CH$_2$— | NMR*: 3.85 (s, 3H) |
| 81 | 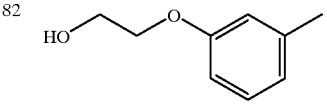 | O | F | N | —CH$_2$—CH$_2$— | NMR*: 3.80 (s, 3H) |
| 82 |  | O | F | N | —CH$_2$—CH$_2$— | NMR*: 3.90 (s, 3H) |

TABLE 1-continued (I)

[Structure: pyrimidine with R-Q substituent, X, linked via O to phenyl bearing C(=E-O-CH3)-oxadiazoline ring with A bridge]

| Ex. No. | R | Q | X | E | A | Phys. data |
|---|---|---|---|---|---|---|
| 83 | 2-(H2N-C(O))-phenyl | O | F | N | —CH2—CH2— | m.p.: >200° C. |
| 84 | 2-(CH(CH3)CH2CH3)-phenyl | O | F | N | —CH2—CH2— | NMR*: 3.85 (s, 3H) |
| 85 | 2-((5,6-dihydro-1,4,2-dioxazin-3-yl)methyl)-phenyl | O | F | N | —CH2—CH2— | NMR*: 3.85 (s, 3H) |
| 86 | 2-(C(CH3)=N-NH-CH3)-phenyl | O | F | N | —CH2—CH2— | NMR*: 3.85 (s, 3H) |
| 87 | 2-Cl-phenyl | O | Cl | N | —CH2—CH2— | NMR*: 3.85 (s, 3H) |
| 88 | phenyl | O | Cl | N | —CH2—CH2— | NMR*: 3.90 (s, 3H) |
| 89 | 2-CH3-phenyl | O | Cl | N | —CH2—CH2— | NMR*: 3.85 (s, 3H) |
| 90 | 2-F-phenyl | O | Cl | N | —CH2—CH2— | NMR*: 3.85 (s, 3H) |

*The 1H NMR spectra were recorded in deuterochloroform (CDCl3) or hexadeuterodimethyl sulphoxide (DMSO-d6) using tetramethylsilane (TMS) as the internal standard. The data given is the chemical shift as δ value in ppm.

Preparation of the starting compounds of Formula (IIa):

Example (IIa-1)

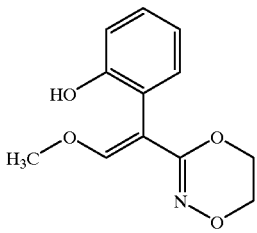

Process a-1)

7.5 g (0.0235 mol) of 3-{1-[2-(tetrahydropyran-2-yloxy)-phenyl]-2-(methoxyethen--yl}-5,6-dihydro-1,4,2-dioxazine are stirred for 16 hours at 20° C. in 20 ml of methanol together with 0.15 g of acidic ion-exchanger resin. The ion-exchanger resin is filtered off and the filtrate is concentrated under reduced pressure. The residue is chromatographed on silica gel using cyclohexane/ethyl acetate (1:1). 1 g (18% of theory) of 3-[1-(2-hydroxyphenyl)-2-methoxyethen-1-yl]-5,6-dihydro-1,4,2-dioxazine.

$^1$H NMR spectrum (CDCl$_3$/TMS): δ=3.794 (3H); 4.102–4.130 (2H); 4.383–4.411 (1H); 6.846 1H); 6.885–6.994 (2H); 7.157–7.260 (2H) ppm.

Preparation of the starting materials of Formula (III):

Example (III-1)

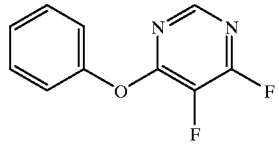

A solution of 42.4 g (0.45 mol) of phenol and 50.4 g (0.45 mol) of potassium tert-butoxide in 400 ml of tetrahydrofuran is added dropwise at 0° C. to a solution of 80 g (0.6 mol) of 4,5,6-trifluoropyrimidine in 1 l of tetrahydrofuran. When the addition was complete, the reaction mixture was stirred for 30 minutes at 0° C. and then poured into water and extracted using ethyl acetate. The organic phase is dried over sodium sulphate and concentrated in vacuo, and the residue is stirred with low-boiling petroleum ether. 63.8 g (68.1% of theory) of 4-phenoxy-5,6-difluoropyrimidine of melting point 65–66° C. are obtained.

The compounds of the formula are obtained analogously to Example (III-1).

| Ex. | R | Q | X | Y$^1$ | Phys. data |
|---|---|---|---|---|---|
| III-2 | 2-chlorobenzyl | O | F | F | m.p. 91° C./ 0.6 mbar Log P 3.20 |
| III-3 | indanyl-methyl | O | F | F | Log P 3.74 |
| III-4 | 2-allyloxybenzyl | O | F | F | Log P 3.32 |
| III-5 | 2-propenylbenzyl | O | F | F | Log P 3.66 |
| III-6 | 2-methylbenzyl | O | F | F | |
| III-7 | 2-ethylbenzyl | O | F | F | |
| III-8 | 2-fluorobenzyl | O | F | F | |
| III-9 | 2-bromobenzyl | O | F | F | |

-continued

R—Q pyrimidine with X and Y¹ substituents

| Ex. | R | Q | X | Y¹ | Phys. data |
|---|---|---|---|---|---|
| III-10 | 2-methyl-6-CF₃-phenyl | O | F | F | |
| III-11 | 2-methyl-6-CN-phenyl | O | F | F | |
| III-12 | 2-methyl-6-OCHF₂-phenyl | O | F | F | |
| III-13 | 2-methyl-6-OCF₃-phenyl | O | F | F | |
| III-14 | 2,3-dimethyl-phenyl | O | F | F | |
| III-15 | 2-methyl-5,6-dichloro-phenyl | O | F | F | |
| III-16 | 2-methyl-3-F-5-Cl-phenyl | O | F | F | |
| III-17 | 2-methyl-6-allyl-phenyl | O | F | F | |

-continued

R—Q pyrimidine with X and Y¹ substituents

| Ex. | R | Q | X | Y¹ | Phys. data |
|---|---|---|---|---|---|
| III-18 | 2-methyl-6-NO₂-phenyl | O | F | F | |
| III-19 | 2,3,4-trimethyl-phenyl (CH₃ groups) | O | F | F | |
| III-20 | 2-methyl-6-(C(CH₃)=N-OCH₃)-phenyl | O | F | F | |
| III-21 | 2-methyl-5,6-dichloro-phenyl | S | F | F | |

Preparation of the starting materials of Formula (IV):

Example (IV-1)

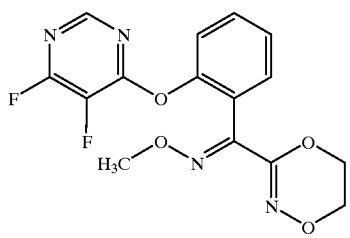

Process b-1)

A solution of 47.2 g (0.2 mol) of 3-[1-(2-hydroxyphenyl)-1-methoximino)-methyl]-5,6-dihydro-1,4,2-dioxazine (WO-A 9504728) in 1 l of tetrahydrofuran is treated, at 0° C., first with 29.3 g (0.22 mol) of 4,5,6-trifluoropyrimidine and subsequently with 6.0 g (0.2 mol) of sodium hydride (80% suspension in mineral oil), a little at a time. The mixture is stirred for 3 hours at 0° C. and subsequently overnight without further cooling. The residue is taken up in ethyl acetate and washed repeatedly with water. The organic phase is dried over sodium sulphate and reconcentrated under reduced pressure, after which a viscous oil remains which crystallizes slowly. 68.7 g (98% of theory) of 3-{1-[2-(4,5-difluoropyrimid-6-yloxy)-phenyl]-1-(methoximino)-methyl}-5,6-dihydro-1,4,2-dioxazine of melting point 98° C. are obtained.

3-{1-[2-(5-chloro-4-fluoropyrimid--6-yloxy)-phenyl]-1-(methoximino)methyl}-5,6-dihydro-1,4,2-dioxazine, Example (IV-2), was obtained analogously to Example (IV-1) in the form of a highly viscous oil.

¹H NMR spectrum (CDCl₃/TMS): δ=3.80 (s, 3H) ppm.

Preparation of the precursors of Formula (VI):

Example (VI-1)

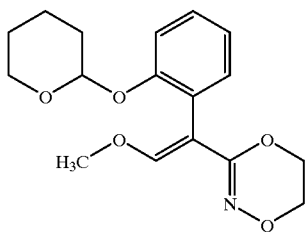

Process a-2)

A mixture of 31.2 g (0.091 mol of methoxymethylene-triphenyl-phosphonium chloride and 10.2 g (0.091 mol) of potassium tert-butoxide in 100 ml of tetrahydrofuran is stirred for 20 minutes at 20° C. A solution of 13.3 g (0.0457 mol) of 3-[2-(tetrahydropyran-2-yloxy)-benzoyl]-5,6-dihydro-1,4,2-dioxazine in 100 ml of tetrahydrofuran is then added, and the mixture is refluxed at the boil for 12 hours. The mixture is concentrated under reduced pressure and the residue is partitioned between water and ethyl acetate. The organic phase is separated off and dried over sodium sulphate. The residue is chromatographed on silica gel using cyclohexane/ethyl acetate (1:1) 9.2 g (63% of theory) of 3-{1-[2-(tetrahyropyran-2-yloxy)-phenyl]-2-(methoxyethen-1-yl}-5,6-dihydro-1,4,2-dioxazine are obtained.

¹H NMR spectrum (CDCl₃/TMS): δ=1.5–1.92 (6H); 3.5–4.0 (2H); 3.730 (3H); 4.056–4.111 (2H); 4.295–4,.325 (2H); 5.410/5.420 (1H); 6.963 (1H); 6.950–7.461 (4H) ppm.

Preparation of the precursors of Formula (VII):

Example (VII-1)

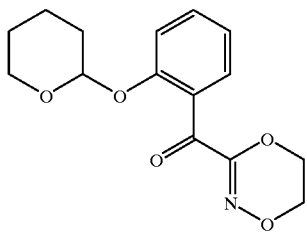

Process a-3)

5 g (0.0193 mol) of 1-(tetrahydropyran-2-yloxy)-2-bromobenzene (Synthesis 1987, page 951) are dissolved in 20 ml of tetrahydrofuran, and the solution is cooled to −40° C. First, 10.8 g (0.0388 mol) of N-butyllithium (23% strength solution in hexane) and then a 50% strength solution of 7.2 g (0.0195 mol) of 1-(5,6-dihydro-1,4,2-dioxazin-3-yl)-1-(pyrrolidin-1-yl)-methanone in tetrahydrofuran are added dropwise at this temperature, and the mixture is stirred for 10 minutes at −40° C. A solution of 4.2 g (0.0785 mol) of ammonium chloride in 25 ml of water is then added dropwise, diethyl ether is added, the organic phase is separated off, and the aqueous phase is extracted repeatedly using diethyl ether. The combined organic phases are dried over sodium sulphate and concentrated under reduced pressure. The residue crystallizes upon trituration with pentane. The crystals are filtered off and washed twice using 5 ml of diisopropyl ether. 2.4 g (35.8% of theory) of 3-[2-(tetrahydropyran-2-yloxy)-benzoyl]-5,6-dihydro-1,4,2-dioxazine (content according to HPLC analysis: 84%) are obtained.

¹H NMR spectrum (CDCl₃/TMS): δ=1.565–1.954 (6H); 3.54–3.68 (1H); 3.78–4.0 (1H); 4.154–4.354 (2H); 4.448–4.510 (2H); 5.512 (1H); 7.004–7.056 (1H); 7.199/−7.227 (1H); 7.408–7.463 (2H) ppm.

Preparation of the precursors of Formula (IX):

Example (IX-1)

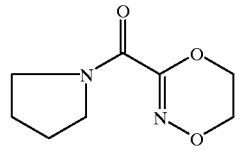

Process a-4)

44.9 g (0.8 mol) of potassium hydroxide are dissolved in 107 ml of methanol, 27.8 g (0.4 mol) of hydroxylammonium chloride are dissolved in 180 ml of methanol, and the two solutions are combined at 35° C. to 40° C. Then, 34.2 g (0.2 mol) of ethyl oxopyrrolidin-1-ylacetate (EP-A 469889) are added at 10 to 20° C., and the mixture is stirred for 30 minutes at 20° C. 27.6 g (0.2 mol) of potassium carbonate and 169.1 g (0.9 mol) of dibromoethane are subsequently added, and the mixture is boiled for 4 hours under reflux. The salts are removed by filtration, the filtrate is concentrated under reduced pressure, the residue is taken up in 600 ml of ethyl acetate, and the organic phase is washed in succession with 50 ml of saturated aqueous sodium chloride solution and with 50 ml of semi-saturated aqueous sodium chloride solution. The organic phase is dried over sodium sulphate, and the solvent is distilled off in vacuo, finally under a high vacuum at 2 Torr and 60° C. 20.9 g (52.2% of theory) of 1-(5,6-dihydro-1,4,2-dioxazin-3-yl)-1-(pyrrolidin-1-yl)-methanone (content according to HPLC analysis: 92%).

¹H NMR spectrum (CDCl₃/TMS): δ=1,841–1,978 (4H); 3.491–3.547 (2H); 3.709–3.793 (2H); 4.166–4.194 (2H); 4.460–4.487 (2H) ppm.

Preparation of the precursors of Formula (XIII):

Example (XIII-1)

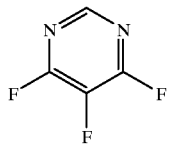

A mixture of 609 g of potassium fluoride in 2.3 l of sulpholane is dried by distilling off 500 ml of liquid at 145° C. and 20 mbar. 1054 g of 5-chloro-4,6-difluoropyrimidine DE-A 3843558) and 25 g of tetraphenylphosphonium bromide are subsequently added, 5 bar of nitrogen is injected and the mixture is stirred for 24 hours at 240° C., during which process the pressure rises to 11 bar. The reaction mixture is cooled to 80° C. and the pressure is released. The mixture is now reheated slowly under atmospheric pressure, during which process the product distills off. When the bottom temperature has reached 200° C., the pressure is reduced to 150 mbar to accelerate the distillation and to obtain further product. In total, 664 g (70.7% of theory) of 4,5,6-trifluoropyrimidine of boiling point 86 to 87° C. are obtained.

Use Examples

Example A
Phytophthora Test (tomato)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of Phytophthora infestans.

The plants are placed in an incubation cabin at about 20° C. and 100% relative atmospheric humidity.

The test is evaluated 3 days after inoculation.

In this test, an efficacy of over 90% is shown, for example, by the compounds of Preparation Examples (1), (2), (3), (6), (8), (10), (17), (40), (41), (43), (47), (49), (55), (63), (76), (77) and (78) at an active compound concentration of 100 ppm.

Example B
Plasmopara Test (vines)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of Plasmopara viticola and then remain in a humidity chamber at 20 to 22° C. and 100% relative atmospheric humidity for 1 day. The plants are then placed in a greenhouse at 21° C. and about 90% atmospheric humidity for 5 days. The plants are then moistened and placed in a humidity chamber for 1 day.

The test is evaluated 6 days after inoculation.

In this test, an efficacy of up to 100% is shown, for example, by the compounds of Preparation Examples (1), (2), (3), (4), (5), (6), (8), (10), (11), (14), (15), (16), (17), (18), (22), (23), (26), (28), (32), (33), (38), (39), (40), (41), (43), (45), (47), (48), (49), (53), (55), (63), (76), (77) and (78) at an exemplary active compound concentration of 100 ppm.

Example C
Sphaerotheca Test (cucumber)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are dusted with conidia of the fungus Sphaerotheca fuliginea.

The plants are then placed in a greenhouse at 23 to 24° C. and at a relative atmospheric humidity of about 75%.

The test is evaluated 10 days after inoculation.

In this test, an efficacy of up to 100% is shown, for example, by the compounds of Preparation Examples (1), (2), (3), (8), (10), (13), (15), (17), (22), (23), (26), (28), (32), (37), (41), (47), (48) and (49) at an active compound concentration of 100 ppm.

Example D
Venturia Test (apple)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous conidia suspension of the pathogen causing apple scab (Venturia inaequalis) and then remain in an incubation cabin at 20° C. and 100% relative atmospheric humidity for 1 day.

The plants are then placed in a greenhouse at 20° C. and a relative atmospheric humidity of about 70%.

The test is evaluated 12 days after inoculation.

In this test, an efficacy of up to 100% is shown, for example, by the compounds of Preparation Examples (1), (2), (3), (4), (5), (6), (8), (10), (11), (13), (14), (15), (16), (17), (18), (22), (26), (28), (32), (33), (37), (38), (39), (41), (43), (45), (47), (48), (49), (53), (55), (63), (77) and (78) at an active compound concentration of 10 ppm.

Example E
Erysiphe Test (barley)/protective

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate indicated.

After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

The test is evaluated 7 days after the inoculation.

In this test, an efficacy of 100% in comparison with the untreated control is shown, for example, by compound (59) at an application rate of active compound of 250 g/ha.

Example F

Erysiphe test (barley)/curative

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp. hordei. 48 hours after inoculation, the plants are sprayed with the preparation of active compound at the application rate indicated. The plants are placed in a greenhouse at a temperature of about 20° C. and a relative atmospheric humidity of about 80%, in order to promote the development of powdery mildew pustules.

The test is evaluated 7 days after the inoculation.

In this test, an efficacy of 100% in comparison with the untreated control is shown, for example, by the compounds of Preparation Examples (1) and (6) at an application rate of active compound of 250 g/ha.

Example G

Fusarium nivale (var. majus) test (wheat)/protective

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate indicated.

After the spray coating has dried on, the plants are sprayed with a conidia suspension of Fusarium nivale var. majus.

The plants are placed in a greenhouse at a temperature of about 15° C. and a relative atmospheric humidity of about 100%, under translucent incubation hoods.

The test is evaluated 4 days after inoculation.

In this test, an efficacy of 100% in comparison with the untreated control is shown, for example, by the compounds of Preparation Examples (8), (11), (14), (15), (24), (33), (41), (42) and (55) at an exemplary application rate of active compound of 250 g/ha.

Example H

Fusarium nivale (var. majus) test (wheat)/curative

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of Fusarium nivale var. majus.

The plants remain in an incubation cabin at 15° C. and a relative atmospheric humidity of 100% for 24 hours. The plants are subsequently sprayed with the preparation of the active compound at the application rate indicated.

After the spray coating has dried on, the plants remain in a greenhouse under translucent incubation hoods at a temperature of about 15° C. and a relative atmospheric humidity of about 100%.

The test is evaluated 4 days after inoculation.

In this test, an efficacy of 100% in comparison with the untreated control is shown, for example, by the compound of Preparation Examples (43) at an exemplary application rate of active compound of 250 g/ha.

Example I

Fusarium nivale (var. nivale) test (wheat)/protective

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate indicated.

After the spray coating has dried on, the plants are sprayed with a conidia suspension of Fusarium nivale var. nivale.

The plants are placed in a greenhouse at a temperature of about 15° C. and a relative atmospheric humidity of about 100% under translucent incubation hoods.

The test is evaluated 4 days after inoculation.

In this test, an efficacy of 100% in comparison with the untreated control is shown, for example, by the compounds of Preparation Examples (10), (11), (15), (24), (32), (34), (43) and (55) at an exemplary application rate of active compound of 250 g/ha.

Example K

Fusarium nivale (var. nivale) test (wheat)/curative

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of Fusarium nivale var. nivale.

The plants remain in an incubation cabin at 15° C. and a relative atmospheric humidity of 100% for 24 hours. The plants are subsequently sprayed with the preparation of the active compound until dew-moist.

After the spray coating has dried on, the plants remain in a greenhouse under translucent incubation hoods at a temperature of about 15° C. and a relative atmospheric humidity of about 100%.

The test is evaluated 4 days after inoculation.

In this test, an efficacy of 100% in comparison with the untreated control is shown, for example, by the compounds of Preparation Examples (24), (30), (31), (34) and (43) at an exemplary application rate of active compound of 250 g/ha.

Example L

Pseudocercosporella herpotrichoides test (wheat)/protective

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with the preparation of the active compound at the application rate indicated. After the spray coating has dried on, the plants are inoculated on the stem base with spores of Pseudocercosporella herpotrichoides.

The plants are placed in a greenhouse at a temperature of about 10° C. and a relative atmospheric humidity of about 80%.

The test is evaluated 21 days after inoculation.

In this test, an efficacy of 100% in comparison with the untreated control is shown, for example, by the compounds of Preparation Examples (15), (69) and (71) at an application rate of active compound of 250 g/ha.

Example M

Puccinia test (wheat)/protective

Solvent: 10 parts by weight of N-methylpyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound at the application rate indicated. The plants remain in an incubation cabin at 20° C. and 100% relative atmospheric humidity for 24 hours.

The plants are placed in a greenhouse at a temperature of about 20° C. and a relative atmospheric humidity of about 80% to promote the development of rust pustules.

The test is evaluated 10 days after the inoculation.

In this test, an efficacy of 100% in comparison with the untreated control is shown, for example, by the compounds of Preparation Examples (6) and (17) at an application rate of active compound of 250 g/ha.

Example N

Pyricularia test (rice)/protective

Solvent: 12.5 parts by weight of acetone

Emulsifier: 0.3 part by weight of alkylaryl polyglycol ether

To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dew-moist. 1 day after the spray coating has dried on, the plants are inoculated with an aqueous spore suspension of Pyricularia oryzae. The plants are then placed in a greenhouse at 25° C. and a relative atmospheric humidity of about 100%.

The disease level is evaluated 4 days after inoculation.

An efficacy of up to 100% in comparison with the untreated control is shown, in this test, for example by the compound of Preparation Examples (2), (16), (17), (18), (19), (23), (24), (30), (32), (35), (41) and (48) at a concentration of active compound of 0.05%.

What is claimed is:

1. Compound of formula (I)

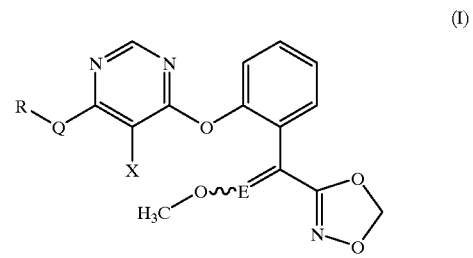

in which
A represents optionally substituted alkanediyl,
R represents in each case optionally substituted cycloalkyl, aryl or benzo-fused heterocyclyl,
E represents —CH= or nitrogen,
Q represents oxygen, sulphur, —CH$_2$—O—, a single bond, or a nitrogen atom which is optionally substituted by alkyl, and
X represents halogen.

2. Compounds of the formula (I) according to claim 1 in which
A represents alkanediyl having 1 to 5 carbon atoms which is optionally substituted by halogen,
R represents cycloalkyl having 3 to 7 carbon atoms which is optionally monosubstituted to disubstituted by halogen, alkyl or hydroxyl;
or represents benzodioxanyl of the formula

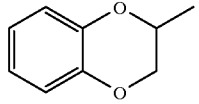

which is optionally substituted by alkyl having 1 to 4 carbon atoms;
or represents phenyl or naphthyl, each of which is optionally monosubstituted to tetrasubstituted by identical or different substituents selected from the group consisting of:
halogen, cyano, nitro, amino, hydroxyl, formyl, carboxyl, carbamoyl, thiocarbamoyl;
straight-chain or branched alkyl, hydroxyalkyl, oxoalkyl, alkoxy, alkoxyalkyl, alkylthioalkyl, dialkoxyalkyl, alkylthio, alkylsulphinyl, or alkylsulphonyl, each of which has 1 to 8 carbon atoms,
straight-chain or branched alkenyl or alkenyloxy, each of which has 2 to 6 carbon atoms;
straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;
straight-chain or branched halogenalkenyl or halogenoalkenyloxy, each of which has 2 to 6 carbon atoms and 1 to 11 idential or different halogen atoms;
straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkenylcarbonyl, each of which has 1 to 6 carbon atoms in the respective hydrocarbon chains;

cycloalkyl or cycloalkyloxy, each of which has 3 to 6 carbon atoms;
alkylene having 3 or 4 carbon atoms, oxyalkylene having 2 or 3 carbon atoms or dioxyalkylene having 1 to 2 carbon atoms, in each case optionally monosubstituted or tetrasubstituted by identical or different selected from the group consisting of fluorine, chlorine, oxo, methyl, trifluoromethyl or ethyl;
or a group

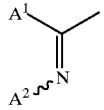

where
A¹ represents hydrogen, hydroxyl or alkyl having 1 to 4 or cycloalkyl having 1 to 6 carbon atoms and
A² represents hydroxyl, amino, methylamino, phenyl, benzyl, or represents alkyl or alkoxy having 1 to 4 carbon atoms, each of which is optionally substituted by cyano, hydroxyl, alkoxy, alkylthio, alkylamino, dialkylamino or phenyl, or represents alkenyloxy or alkenyloxy, each of which has 2 to 4 carbon atoms,
and also phenyl, phenoxy, phenylthio, benzoyl, benzoylethenyl, cinnamoyl, heterocyclyl, phenylalkyl, phenylalkyloxy, phenylalkylthio or heterocyclalkyl, each of which has 1 to 3 carbon atoms in the respective alkyl moieties and each of which is optionally monosubstituted to trisubstituted in the cyclic moiety by halogen and/or straight-chain or branched alkyl or alkoxy having 1 to 4 carbon atoms,
E represents —CH= or nitrogen,
Q represents oxygen, sulphur, a single bond or a nitrogen atom which is optionally substituted by methyl, ethyl or n- or i-propyl and
X represents fluorine, chlorine, bromine or iodine.

3. Compounds of the formula (I) according to claim 1 in which
A represents methylene, ethane-1,1-diyl, ethane-1,2-diyl, propane-1,1-diyl, propane-1,2-diyl, propane-1,3-diyl, butane-1,1-diyl, butane-1,2-diyl, butane-1,3-diyl or butane-2,2-diyl, each of which is optionally substituted by fluorine or chlorine,
R represents cyclopentyl or cyclohexyl, each of which is optionally monosubstituted to disubstituted by fluorine, chlorine, methyl, ethyl or hydroxyl;
or represents benzodioxanyl of the formula

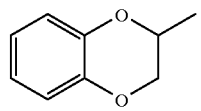

which is optionally substituted by methyl or ethyl;
or represents phenyl or naphthyl, each of which is optionally monosubstituted to tetrasubstituted by identical or different substituents selected from the group consisting of:
fluorine, chlorine, bromine, iodine, cyano, nitro, amino, hydroxyl, formyl, carboxyl, carbamoyl, thiocarbamoyl,
methyl, ethyl, n- or i-propyl, n-, i-, s- or t-butyl, 1-, 2-, 3-, neopentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl,
methoxy, ethoxy, n- or i-propoxy,
methylthio, ethylthio, n- or i-propylthio, methylsulphinyl, ethylsulphinyl, methylsulphonyl or ethylsulphonyl,
vinyl, allyl, 2-methylallyl, propen-1-yl, crotonyl, propargyl, vinyloxy, allyloxy, 2-methylallyloxy, propen-1-yloxy, crotonyloxy, propargyloxy,
trifluoromethyl, trifluoroethyl, difluoromethoxy, trifluoromethoxy, difluorochloromethoxy, trifluoroethoxy, difluoromethylthio, trifluoromethylthio, difluorochloromethylio, trifluoromethylsulphinyl or trifluoromethylsulphonyl,
methylamino, ethylamino, n- or i-propylamino, dimethylamino, diethylamino,
acetyl, propionyl, methoxycarbonyl, ethoxycarbonyl, methylaminocarbonyl, ethylaminocarbonyl, dimethylaiminocarbonyl, diethylaminocarbonyl, dimethylaminocarbonyloxy, diethylaminocarbonyloxy, benzylaminocarbonyl, acryloyl, propioloyl,
cyclopentyl, cyclohexyl,
in each case divalent propanediyl, ethyleneoxy, methylenedioxy, ethylenedioxy, each of which is optionally monosubstituted to tetrasubstituted by identical or different substituents selected from the group consisting of fluorine, chlorine, oxo, methyl or trifluoromethyl,
or a group

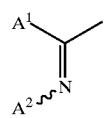

where
A¹ represents hydrogen, methyl or hydroxyl, and
A² represents hydroxyl, methoxy, ethoxy, amino, methylamino, phenyl, benzyl or hydroxyethyl, and
phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxazin-2-yl, benzimidazol-2-yl, dioxol-2-yl, oxadiazolyl, each of which is optionally monosubstituted to trisubstituted in the cyclic moiety by halogen and/or straight-chain or branched alkyl or alkoxy having 1 to 4 carbon atoms,
E represents —CH= or nitrogen,
Q represents oxygen, sulphur, a single bond or a nitrogen atom which is optionally substituted by methyl, and
X represents fluorine or chlorine.

4. Process for the preparation of a pesticidal composition, said process comprising mixing at least one compound of the formula (I) according to claim 1 with an extender and/or a surfactant.

5. Process for the preparation of compounds of the formula (I) according to claim 1, wherein a) hydroxy compounds of the general formula (II)

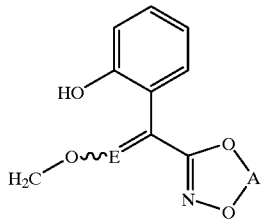
(II)

in which
A and E have the meanings given in claim 1, are reacted with a substituted halogenopyrimidine of the general formula (III)

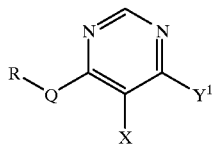
(III)

in which
R, Q and X have the meanings given in claim 1 and Y¹ represents halogen,
if appropriate in the presence of a diluent, if appropriate in the presence of an acid acceptor and if appropriate in the presence of a catalyst, or wherein b) phenoxypyrimidines of the general formula (IV)

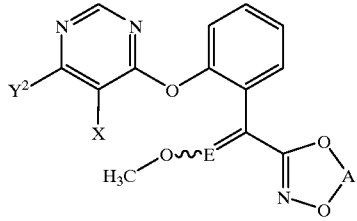
(IV)

in which
A, E and X have the meanings given in claim 1, and Y² represents halogen
are reacted with a cyclic compound of the general formula (V)

R—Q—H (V)

in which
R and Q have the meanings given in claim 1,
if appropriate in the presence of a diluent, if appropriate in the presence of an acid acceptor and if appropriate in the presence of a catalyst.

6. A pesticidal composition comprising a pesticidally effective amount of at least one compound of the formula (I) according to claim 1 and an extender.

7. A method of controlling pests comprising applying a pesticidally effective amount of at least one compound of the formula (I) according to claim 1 to the pests and/or their environment.

8. The compound of the formula (I) according to claim 1, which is 3-{1-[2-(4-<2-chlorophenoxy>5-fluoropyrimid-6-yloxy)-phenyl-1-(methoximino)-methyl}-5,6-dihydro-1,4,2-di-oxazine, having the formula:

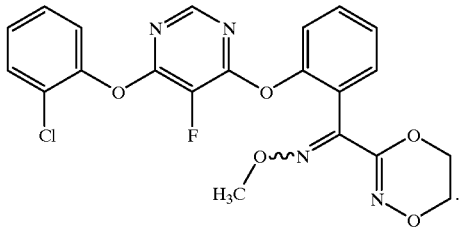

9. A pesticidal composition comprising a pesticidally effective amount of at least one compound of the formula (I) according to claim 8 and an extender.

10. A method of controlling pests comprising applying a pesticidally effective amount of at least one compound of the formula (I) according to claim 8 to the pests and/or their environment.

* * * * *

UNITED STATES PATENT AND TRADEMARK OFFICE
CERTIFICATE OF CORRECTION

PATENT NO. : 6,103,717
DATED : August 15, 2000
INVENTOR(S) : Heinemann et al.

Page 1 of 2

It is certified that error appears in the above-identified patent and that said Letters Patent is hereby corrected as shown below:

Column 1 and Columns 17-40,
Please substitute each occurrence of the structure depicted by formula(I):

"

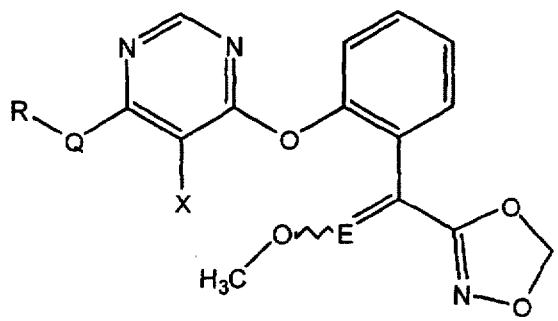

"

with the structure below:

-----

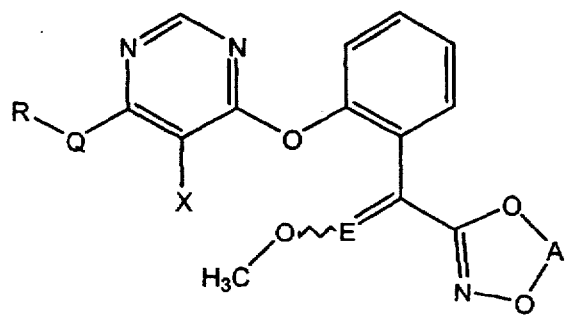

-----.

UNITED STATES PATENT AND TRADEMARK OFFICE
CERTIFICATE OF CORRECTION

PATENT NO. : 6,103,717
DATED : August 15, 2000
INVENTOR(S) : Heinemann et al.

Page 2 of 2

It is certified that error appears in the above-identified patent and that said Letters Patent is hereby corrected as shown below:

<u>Column 52, claim 1,</u>
Please subsitute each occurrence of the structure depicted by formula(I):

"

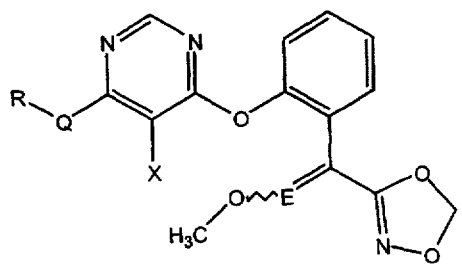

"

with the structure below:
-------------

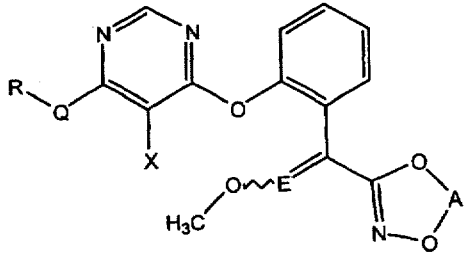

-------------.

Signed and Sealed this

Eleventh Day of December, 2001

Attest:

NICHOLAS P. GODICI
Attesting Officer    Acting Director of the United States Patent and Trademark Office